United States Patent
Plumptre (10) Patent No.: US 8,986,260 B2
(45) Date of Patent: Mar. 24, 2015

(54) DOSE SETTING MECHANISM AND INJECTION DEVICE

(75) Inventor: David Aubrey Plumptre, Worcestershire (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 14/007,086

(22) PCT Filed: Mar. 22, 2012

(86) PCT No.: PCT/EP2012/055058
§ 371 (c)(1),
(2), (4) Date: Sep. 24, 2013

(87) PCT Pub. No.: WO2012/130705
PCT Pub. Date: Oct. 4, 2012

(65) Prior Publication Data
US 2014/0025016 A1    Jan. 23, 2014

(30) Foreign Application Priority Data
Mar. 25, 2011 (EP) ..................................... 11159758

(51) Int. Cl.
*A61M 5/315* (2006.01)
*A61M 5/24* (2006.01)

(52) U.S. Cl.
CPC ............. *A61M 5/31533* (2013.01); *A61M 5/24* (2013.01); *A61M 5/31525* (2013.01); *A61M 5/31566* (2013.01)
USPC .......................................... 604/209; 604/207

(58) Field of Classification Search
CPC ..................... A61M 5/31533; A61M 5/31525; A61M 5/31535; A61M 5/31565
USPC .......................... 604/209, 207, 208, 210, 211
See application file for complete search history.

(56) References Cited

U.S. PATENT DOCUMENTS

2013/0245558 A1*  9/2013  Holmqvist .................... 604/189

FOREIGN PATENT DOCUMENTS

| EP | 1645301 A1 | 4/2006 |
|---|---|---|
| WO | 9114467 A1 | 10/1991 |
| WO | 2010139637 A1 | 12/2010 |
| WO | 2011039233 A1 | 4/2011 |

* cited by examiner

*Primary Examiner* — Bhisma Mehta
*Assistant Examiner* — Hamza Darb
(74) *Attorney, Agent, or Firm* — McDonnell Boehnen Hulbert & Berghoff LLP (57) ABSTRACT

A dose setting mechanism comprising a dose setting member and a drive member for driving a piston rod in a distal direction during dose dispensing. The drive member comprises a proximal drive member and a distal drive member. A first clutch releasably coupling the proximal drive member and the distal drive member. A spring means biases the proximal drive member and the distal drive member in the coupled state during dose setting and dose dispensing. Engaging means are provided associated to the proximal drive member and to the dose setting member, wherein the engaging means are designed and arranged such that the proximal drive member entrains the dose setting member in the distal direction during dose setting but allows a relative axial movement of the proximal drive member with respect to the dose setting member in the proximal direction.

13 Claims, 4 Drawing Sheets

DOSE SETTING MECHANISM AND INJECTION DEVICE

CROSS REFERENCE TO RELATED APPLICATIONS

The present application is a U.S. National Phase Application pursuant to 35 U.S.C. §371 of International Application No. PCT/EP2012/055058 filed Mar. 22, 2012, which claims priority to European Patent Application No. 11159758.9 filed Mar. 25, 2011. The entire disclosure contents of these applications are herewith incorporated by reference into the present application.

FIELD OF INVENTION

The present invention is directed to a dose setting mechanism for a drug delivery device, like a pen-type injector, that provides for administration by injection of medicinal products from a multidose cartridge and where the user can select a variable dose of medicament in incremental steps or units from a given range of doses permitted by the device mechanism. The dose setting mechanism comprises a dose setting member (e.g. a number sleeve) and a drive member (e.g. a drive sleeve). Further components may be provided, for example a housing, a clutch and a clicker. Further, the invention refers to an injection device with such a dose setting mechanism.

In more detail, the invention is directed to a dose setting mechanism for a resettable drug delivery device which uses a two part drive sleeve that should remain coupled during both dialing and dispense and which only decouples when the user presses on the piston rod to reset the device. A resettable drug delivery device allows the user to change or to replace a cartridge containing a medicament and to reset the dose setting mechanism to an initial state allowing dose setting and dose dispensing using the new cartridge.

BACKGROUND

In a reusable pen having a two piece drive sleeve, the two halves of the drive sleeve are coupled during both dialing and dispense but are decoupled to enable the piston rod to reset when a new cartridge is fitted. A potential failure mode of such a design is that if the attached needle is blocked, or if the user forgets to attach a needle, and the user attempts to dispense a dose by pressing a dose button, then the dose button will begin to advance, the number sleeve will begin to rotate (counting downwards from the "set" dose) and the piston rod will begin to advance distally (in the direction of the cartridge), causing the deformable elements of the cartridge, for example a rubber bung and/or a rubber septum closing the needle end of the cartridge, to compress or deform until such time as the pressure from the cartridge bung against the piston rod becomes sufficient to resist the applied user force and the dispensing mechanism will then jam. This will typically occur within a few mm movement of the piston rod (i.e. within a few "units" of the number sleeve display). The increased resistance to movement of the dose button, and the jamming of the dispense mechanism, alerts the user to the fact that the mechanism is not working correctly (i.e. the medicament is not being dispensed), even though the number sleeve will now be displaying a number less than the "set" dose (i.e. the number sleeve appears to display a "partially dispensed" dose). If the user then releases pressure on the dose button, the deformable elements of the cartridge will tend to return to their original state, causing pressure on the piston rod which will cause it to move proximally (in the direction of the dose setting mechanism) which will in turn cause the device to go into a reset mode which will relieve the pressure in the system and will enable the dispensing mechanism to operate again, with the user force required to start the dose button moving again, having returned to the normal operating value, i.e. before the jam occurred. During reset the number sleeve, which is not affected by the resetting of the piston rod, will continue to display the "partially dispensed" dose. If the needle remains blocked, and, in an attempt to complete this undelivered or apparently partially delivered dose, the user repeats this cycle of pressing and releasing the dose button, whilst the device repeatedly jams and self-resets, the number sleeve will appear to be display that the device is dispensing medicament in stages of several units, with the number sleeve eventually returning to display zero units, i.e. the number sleeve appears to display a "completed dose", when in fact no medicament is dispensed.

It is therefore an object of this invention to provide an improved and yet compact dose setting mechanism for a resettable pen device that removes this potential failure mode.

This is obtained by a dose setting mechanism as defined in claim 1. The dose setting mechanism of the present invention can be used in devices which use a two part drive sleeve that remains coupled during both dose dialing and dose dispensing and which only decouples when the user presses on the piston rod to reset the device e.g. replacing a cartridge. A dose setting mechanism according to the present invention comprises a dose setting member, e.g. a number sleeve, a dose button, a drive member, e.g. a drive sleeve, for driving a piston rod in a distal direction during dose dispensing, a first clutch and spring means.

Typically, the drive member comprises a proximal drive member and a distal drive member which are releasably coupled via the first clutch. The spring means are designed for biasing the proximal drive member and the distal drive member in the coupled state such that during dose setting and dose dispensing relative rotation of the two parts of the drive member is not allowed. Preferably, the first clutch rotationally couples the proximal drive member and the distal drive member during dose setting and dose dispensing and rotationally decouples the proximal drive member and the distal drive member during resetting of the mechanism. The operation of the dose button by the user, e.g. during dispense, increases the compression of the spring means, and therefore prevents decoupling of the clutch during dispense when a force is applied to the piston rod.

Further, engaging means are provided which are associated to the proximal drive member and to the dose setting member, respectively. Said engaging means are designed and arranged such that the proximal drive member entrains the dose setting member in the distal direction during dose dispensing but allows a relative axial movement of the proximal drive member with respect to the dose setting member in the proximal direction at all other times. If the mechanism is a resettable mechanism it is preferred that the engaging means, if applicable together with further means, allow a relative axial movement of the proximal drive member with respect to the dose setting member in the proximal direction only when a dose button for transmitting a dispensing force applied by a user to the mechanism is pressed during or following dose dispense, and resists relative axial movement when the dose button is not depressed during reset. In normal, non-dispensing, operation the proximal drive member and the dose setting member will be biased into contact at the engaging means by the force applied by the spring means. According to a preferred embodiment of the invention, the engaging means may comprise hooks provided on fingers protruding from the proximal end of the proximal drive member and a corresponding inwardly protruding flange on the proximal end of the dose setting member.

The above mentioned design of the dose setting mechanism allows the proximal half of the drive sleeve to move proximally with the distal half of the drive sleeve in the event that the dose button is released with residual bung compression, e.g. during the potential failure mode of the user attempting to dispense medicament with a blocked needle. If both halves move together axially then they do not decouple and the device does not enter the reset mode thus avoiding the potential failure mode. In this case if a new, unblocked, needle is fitted, then the spring means, which will have been further compressed by the proximal movement of both halves of the drive member, will cause the whole drive member to be driven distally again, dispensing medicament from the needle and relieving the compression in the cartridge, and restoring the correlation between the displayed dose on the number sleeve and the set dose in the mechanism.

Typically, the engaging means comprise a flange or protrusion provided on the proximal drive member and a corresponding flange or protrusion provided on the dose setting member. Thus, the engaging means are integrally formed on the proximal drive member and the dose setting member, respectively. As an alternative, the engaging means may comprise separate components which are attached to the proximal drive member and/or to the dose setting member.

SUMMARY

According to a preferred embodiment of the invention the dose setting mechanism further comprises a second clutch for releasably coupling the drive member, preferably the proximal drive member, and the dose setting member. Said second clutch may comprise a tubular element having at least one axial groove engaging a spline provided on proximal drive member. Thus, the second clutch is rotationally fixed to the, e.g. proximal, drive member such that the drive member rotates during dose setting if the second clutch is rotated via the dose setting member. The keyed engagement of the drive member and the clutch may be realized by more than a single pair of corresponding spline and groove.

By permitting relative axial movement of the proximal drive member with respect to the dose setting member in the proximal direction, the device resetting following an attempted dispense with a blocked needle is prevented. However, if both proximal and distal halves of the drive member were to move proximally during reset this would also prevent the device from being able to enter the reset mode when a new cartridge is fitted. This is because entering the reset mode requires that the proximal half of the drive sleeve is prevented from proximal axial movement whilst the drive sleeve distal end is decoupled by being driven proximally. Thus, according to a further aspect of the present invention, means are provided for restraining relative axial movement of the proximal drive member with respect to the dose setting member in the proximal direction during resetting of the device. It is preferred to provide the at least one axial groove with a step which is located at a transition from a first portion of the groove having a smaller width to a second portion of the groove having a larger width, wherein the width of the spline is chosen to allow the spline to slide within both portions of the groove. The proximal half of the drive member and the second clutch are rotationally biased such that the spline is in contact with the side of the groove containing the step, i.e. the spline, and hence the proximal half of the drive member, is free to travel in the proximal or distal direction guided in the groove but resists further proximal movement when the end of the spline contacts the step. Thus, the step in the axial groove may prevent proximal movement of the proximal drive member during resetting. Resistance to proximal movement of the proximal half of the drive member is also provided by the frictional forces between the proximal half of the drive member and the second clutch. Under the action of normal resetting forces the resistance to proximal movement of the distal end of the drive member only needs to be sufficient to overcome the friction in the first clutch coupling the distal and proximal halves of the drive member.

Hence, the additional feature of the step overcomes a potential drawback of the device because axial movement of the proximal half of the drive member is prevented during normal device reset when the second clutch is coupled to the dose setting member, whereas, following an attempted dispense with a blocked needle, the second clutch, which is fixed to the dose button, will have been moved distally during dispense, decoupling it from the dose setting member, and so the end of the spline will already be beyond the step of the groove. In the second instance the frictional forces between the proximal half of the drive member and the second clutch will actually assist, rather than resist, proximal movement of the proximal half of the drive member. Further, in the second instance, the friction in the first clutch between the proximal and distal halves of the drive sleeve will be many times higher than in the normal reset case (because the force acting on the piston rod, and hence, via its threaded connection to the drive sleeve distal end, attempting to rotate the drive sleeve distal end resisted by the features of the first clutch, is much higher in the case of the cartridge with blocked needle compared to the normal reset force). Therefore, the friction force in the first clutch is sufficient to ensure the proximal movement of the proximal half of the drive member without the first clutch becoming decoupled.

In normal operation, when the user presses the dose button, the step of the groove in the second clutch must pass the end of the spline on the proximal end of the drive sleeve. At this point the engaging means between the proximal half of the drive member and the dose setting member will prevent the distal movement of the proximal half of the drive sleeve. The resisting force of the step in the second clutch groove and the friction of the second clutch on the proximal half of the drive sleeve will be small relative to the available user force on the dose button. The user may experience a small detent force on the dose button as the step passes over the end of the spline (which may also be an advantageous as it helps to provide positive tactile feedback to the dose button and therefore helps to prevent accidental dispense).

The grooves in the second clutch and spline on the proximal drive member may be swapped over to achieve the same function.

Preferably, the dose setting mechanism according to the present invention further comprises means for biasing and/or holding the spline of the drive member in a defined angular position with respect to the groove of the clutch. This ensures that the steps in the clutch grooves engage with the ends of the drive sleeve proximal end splines so as to prevent the drive sleeve sliding proximally during reset.

According to a further development of this idea, the means for biasing and/or holding the spline comprise a clicker mechanism. Preferably, the clicker mechanism comprises two clicker parts, each provided with corresponding toothed rings on opposing end faces of the two clicker parts. Further corresponding toothed rings may be provided on the other end face of one of the clicker parts and on the opposing face of the second clutch for releasably biasing the second clutch to the clicker. According to one embodiment, the first clicker part has two toothed ring on its end faces as biasing features aligning the second clutch to the first clicker part and clicker features releasably coupling the first clicker part to the second clicker part. The first clicker part is rotationally coupled to a housing component by means of external axial splines on the first clicker and internal axial grooves in the housing. Further, the second clicker part has an axial groove engaging an axial spline on the drive sleeve proximal end to rotationally couple these two components.

A potential drawback of the above described design where the whole mechanism can move proximally relative to the dose setting member and the housing when the dose button is released after dispense with a blocked needle is that the user is subsequently unable to dial up or down, i.e. to amend the set dose. This is because in this condition the proximal drive member is proximally displaced relative to the second clutch and hence the spring means is compressed and therefore the first clicker part and second clicker part are rotationally locked together (as in the dispense condition), which in turn rotationally locks the proximal drive member to the housing. If in this situation the user applies excessive torsion to the dose setting member then, due to the small size of and limited engagement between the splines on the proximal drive member rotationally coupling it to the first clicker part (this limited engagement is due to the limited dose button travel), these splines could fail by plastic deformation, leading to subsequent device failure or dose errors.

A solution to this potential drawback is to form the splines and grooves engaging the proximal drive member and the first clicker part when the dose button is pressed as rounded splines/grooves. In this case, after dispensing with a blocked needle, if the user tries to rotate the dose setting member, the round splines and grooves will resist the rotation and the dialing torque will be significantly higher than the normal torque required to overcome the clicker teeth, and this should provide clear feedback to the user that something is wrong and therefore not to continue to apply greater dialing torque. If the user nevertheless continues to try and dial, applying even greater torque, then, rather than deforming plastically, the rounded splines will bump underneath the rounded grooves in the first clicker part and will not cause permanent damage to the device.

In the needle blocked failure condition, and in the event that the user applies an excessive dialing torsion to the jammed mechanism such that the rounded splines and groove bump over as described, then the second clutch and hence dose button will be engaged with the number sleeve and the device will dial up or down normally except for the very high dialing torque.

As mentioned above, the correct way to overcome this failure mode (i.e. attempting to dispense with a blocked needle) is to replace the blocked needle with a functional needle, allowing medicament to escape through the needle and relieving the compressive loads on the internal mechanism. If the user then proceeds to dispense by pressing on the dose button they will receive the dialed dose.

According to preferred embodiment of the present invention, the dose setting member comprises a dose dial sleeve (or number sleeve) which is rotatable relative to the housing to set a dose. Further, the drive member may comprise a drive sleeve which is movable in a first axial direction relative to the housing member during dose setting and which is movable in a second axial direction relative to the housing member during dose dispensing, which second axial direction is opposite to said first axial direction. Preferably, the movement of the drive sleeve during dose setting includes a translational component and a rotational component, e.g. a movement along a helical path. During dose dispensing it is preferred that the drive sleeve moves only axially, i.e. without any rotational components of the movement.

If the second clutch rotationally couples the dose setting member and the drive member during dose setting and rotationally decouples the dose setting member and the drive member during dose dispensing, the drive member follows a movement of the dose setting member along a helical path during dose setting while the dose setting member is allowed to rotate relative to the drive member during dose dispensing. It is an advantage that the dose setting mechanism requires less force during dose dispensing.

BRIEF DESCRIPTION OF THE DRAWINGS

In the following, the invention will be described by a way of an example and with reference to the schematic drawings in which.

DETAILED DESCRIPTION

Figure 1:
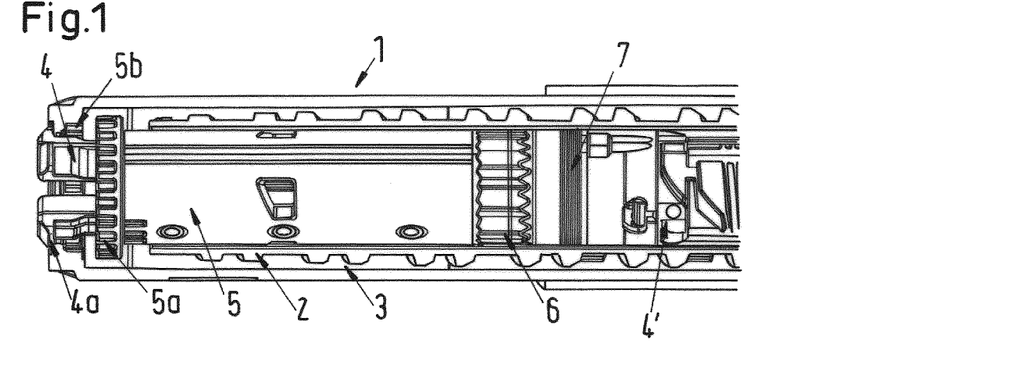
FIG. 1 shows a partial section of a dose setting mechanism with a dose dialed and with the dose button pressed in (i.e. in the dose dispensing mode)
Figures 12, 13, 14:
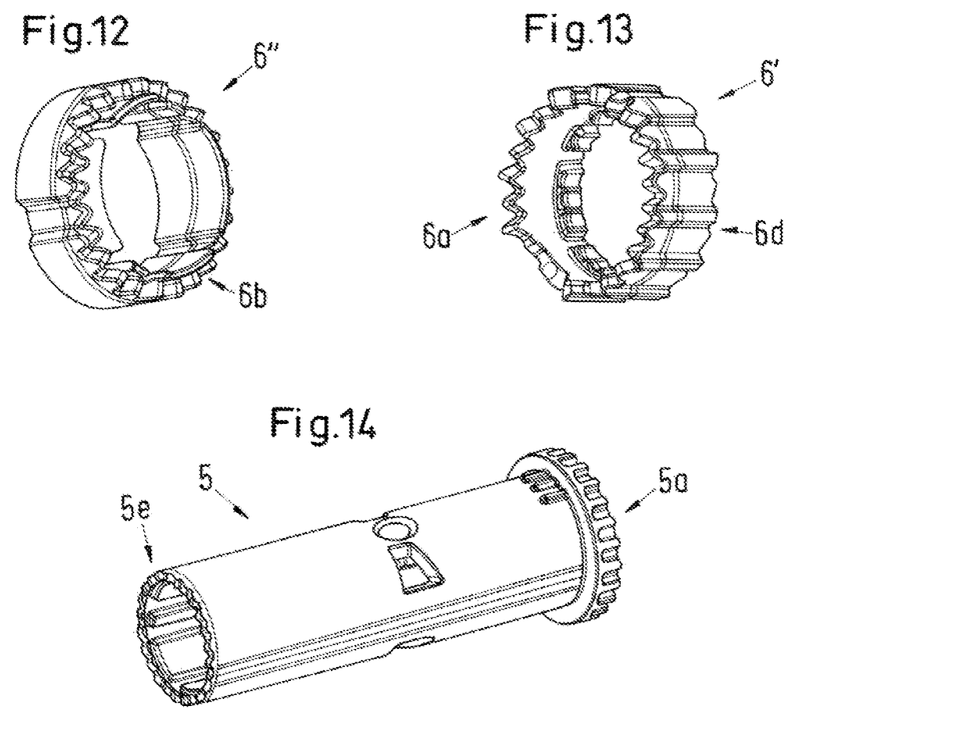
FIG. 12 shows a perspective view of the second clicker component of the dose setting mechanism of FIG. 1.
FIG. 13 shows a perspective view of the first clicker component of the dose setting mechanism of FIG. 1.
FIG. 14 shows a perspective view of the second clutch element of the dose setting mechanism of FIG. 1.
Figure 15:
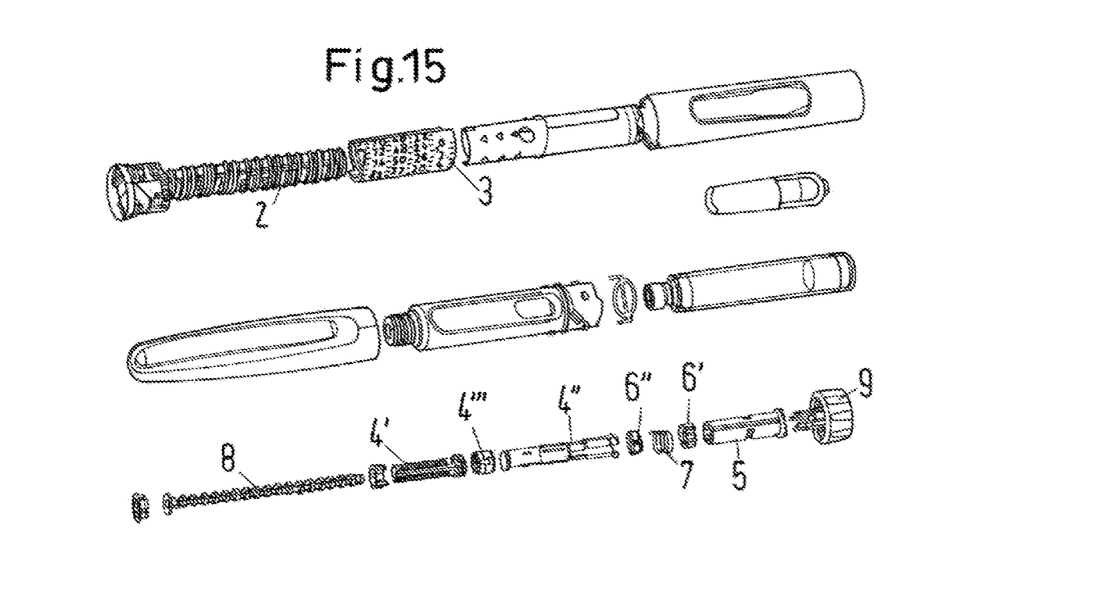
FIG. 15 shows an exploded view of the components of an injection device.

FIG. 1 shows a typical dose setting mechanism 1 of an injection device with a clicker mechanism. The dose setting mechanism comprises an (internal) housing member 2, a dose setting member 3 comprising a dose dial sleeve or number sleeve, a drive member 4 in the form of a drive sleeve, a tubular second clutch element 5 and a clicker 6. The second clutch element 5 is located between the dose setting member 3 and the drive member 4 and is rotationally coupled to the drive member 4 by means of at least one groove and corresponding spline. Further, the second clutch element 5 is axially movable relative to the dose setting member 3 for rotationally coupling and decoupling the dose setting member 3 and the drive member 4. As shown in FIGS. 1 and 14, the second clutch element 5 uses two sets of matching face teeth 5a, 5b which are provided on an inner end face of the dose setting member 3 and a corresponding end face of the tubular second clutch element 5.

In the Figures, a dose setting mechanism is shown where the clicker 6 is split into two parts, first clicker component 6' and second clicker component 6" which are depicted in more detail in FIGS. 12 and 13. The first clicker component 6' is splined to the housing member 2 and therefore must be free to rotate relative to the drive member 4 and second clutch element 5 during dialing.

Clicker teeth 6a, 6b are provided in a similar manner as described above with respect to second clutch element 5, however the teeth 6a, 6b have a much shallower angle compared to teeth 5a, 5b. These clicker teeth in conjunction with the coil spring 7, provide the detents for the dialed dose and the clicks for tactile and audible feedback. In other words, clicker teeth 6a, 6b which are provided on first and second clicker element, respectively, are allowed to ride one over the other during dose setting. First clicker component 6' moves axially by only very small amounts (equal to the height of teeth 6d between the first clicker 6' and second clutch 5) during dialing and therefore it can be rotationally locked to the drive member 4 after only a very small relative axial displacement and well within the axial engagement of the clutch teeth 5a, 5b.

The second clicker component 6" component is always rotationally coupled to the drive member 4 and shuttles axially, alternately compressing and uncompressing the clicker spring 7, as the clicker teeth 6a, 6b ride over one another during dialing.

The spring 7 further serves to provide the necessary axial force to engage clutch teeth 5a on second clutch element 5 (which is splined to the drive member 4 as explained below) with clutch features 5b on the number sleeve 3 at the end of a delivered dose and during subsequent dialing of the next dose. In this way the one spring 7 serves two functions.

Figures 9, 10, 11:
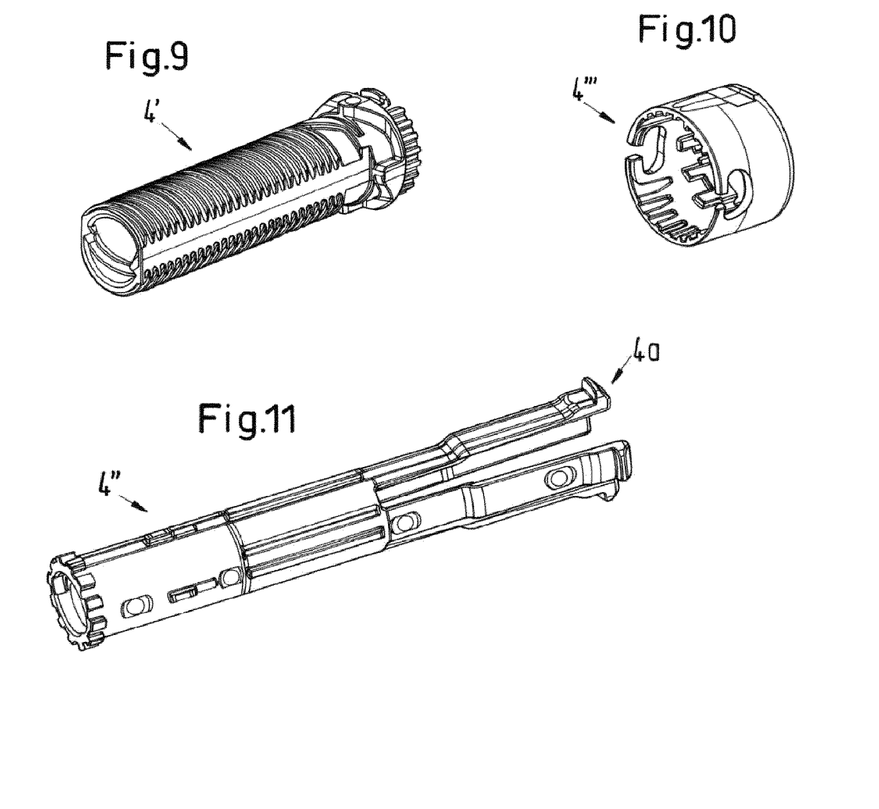
FIG. 9 shows a perspective view of the distal drive member of the dose setting mechanism of FIG. 1.
FIG. 10 shows a perspective view of a coupler of the dose setting mechanism of FIG. 1.
FIG. 11 shows a perspective view of the proximal drive member of the dose setting mechanism of FIG. 1.

The drive member comprises two components, a distal drive member 4' and a proximal drive member 4". As shown in FIG. 9 the distal drive member 4' may be provided with an internal thread engaging a threaded piston rod 8. The proximal drive member 4" which is shown in FIG. 11 is a tubular element (drive sleeve) surrounded by the second clutch element 5 and the clicker mechanism 6. A coupler 4''' as shown in FIG. 10 may be provided attached to distal half 4' of the drive member providing a first clutch to rotationally couple the two drive sleeve halves 4', 4" together during dialing and dose dispensing. The coupler and distal half 4' are provided as separate components for manufacturing reasons only and, once fixed together during device assembly, function as one single component. The coupler 4''' is provided with teeth engaging corresponding teeth on the proximal half 4" of the drive member in the coupled state of the drive member 4, i.e. during dose setting and dose dispensing, this defining the first clutch. During dialing the clicker spring 7 biases the two halves of the drive member into their coupled condition. However, the two halves of the drive member 4 may be decoupled for resetting the device allowing the distal drive member 4', which is threaded to the piston rod 8, to move proximally under the action of the piston rod while the proximal drive member 4" remains fixed within the housing 2 via its splined connection to the clicker mechanism and second clutch.

FIG. 1 shows the device with a button 9 depressed during dose dispensing. This decouples the clutch teeth 5a, 5b between the second clutch element 5 and the number sleeve 3 and compresses the clicker spring 7. Whether or not the clicker spring 7 is compressed to a solid state, the load compressing this spring is sufficient to prevent the clicker face teeth 6a, 6b from disengaging under any dispense loads applied by the user to the button during dispense. These clicker face teeth 6a, 6b therefore rotationally lock the two clicker elements 6', 6". Since the dispense force is transferred directly from spring 7 to the distal drive sleeve 4', with the distal drive sleeve 4' effectively pulling the distal drive sleeve 4" in the distal direction, there is no tendency for the first clutch to decouple the distal and proximal drive sleeve halves 4', 4" during dispense. Further, as the first clicker 6' is splined to the housing member 2 and the second clicker 6" is splined to the distal drive sleeve 4', this effectively locks the entire drive sleeve 4 to the housing member 2 in rotation.

Figure 7:
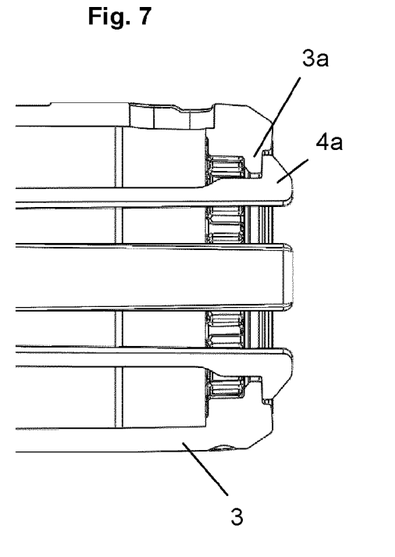
FIG. 7 shows as a sectional view an enlarged detail of the proximal drive member of the dose setting mechanism of FIG. 1, 2 or 3.
Figure 8:
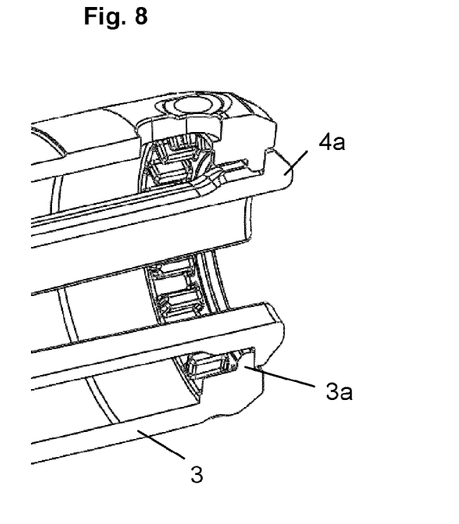
FIG. 8 shows as a perspective view an enlarged detail of the proximal drive member of the dose setting mechanism of FIG. 1, 2 or 3.

The proximal drive member 4" has at its proximal end a flange 4a or collar engaging a corresponding flange or protrusion 3a of the number sleeve 3 to entrain same under the distal movement of the drive member 4" during dose dispensing. As depicted in FIGS. 7 and 8 in more detail, the engaging means may comprise hooks 4a provided on fingers protruding from the proximal end of the proximal drive member 4" and a corresponding inwardly protruding flange 3a on the proximal end of the dose setting member 3.

Figure 2:
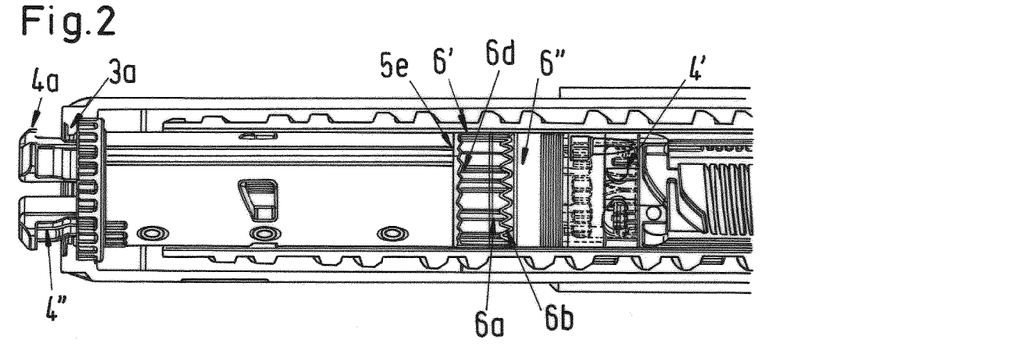
FIG. 2 shows a partial section of the dose setting mechanism of FIG. 1 after releasing the dose button following an attempted dose with a blocked needle (a dose is still dialed)

FIG. 2 shows what happens if the dose button is released whilst there is still a proximal axial force acting on the distal drive member due to compression of the cartridge bung, e.g. resulting from attempting to dispense with a blocked needle. In contrast to the distal direction, where flange 4a of the proximal drive member 4" entrains number sleeve 3, the proximal drive member 4" is free to move in the proximal direction relative to the number sleeve 3. In other words, the proximal drive member 4" is allowed to move proximally together with the distal drive member 4' when the dose button is released with residual compression in the cartridge (e.g. of the cartridge bung and septum). If both halves move together axially then they do not decouple and the device does not enter the reset mode. In this case if a new needle is fitted then the spring 7 will drive the drive sleeve in the distal direction, dispensing medicament until the compressive forces in the cartridge have fully relaxed.

It is preferred to provide an additional feature that allows the resetting of the device 1 when a new cartridge is fitted, i.e. it is preferred to provide an additional feature which does not prevent axial movement of the proximal drive member 4" following dispense with a blocked needle but does block or limit this same movement during normal device reset (and also permits the distal movement of the second clutch 5 relative to the distal drive sleeve 4" during pressing of the dose button to initiate a normal dispense). In the first instance the second clutch 5 is decoupled from the number sleeve 3 and in the second case it is coupled, resulting in different relative axial positions of the second clutch 5 to the proximal drive member 4". Therefore a feature placed between these two parts can be added to allow relative axial movement in the first instance but block or limit this movement in the second instance.

Figure 3:
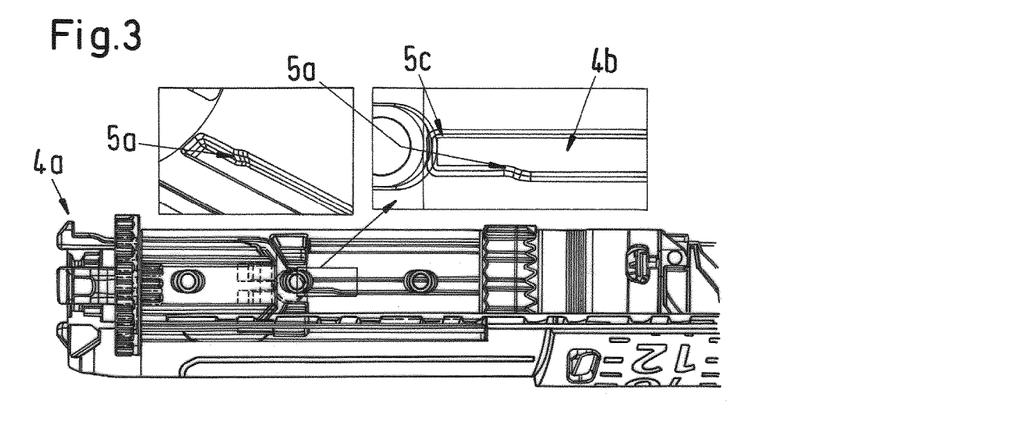
FIG. 3 shows an enlarged detail of the dose setting mechanism of FIG. 1 (still with a dose dialed and with the dose button pressed in)
Figure 4:
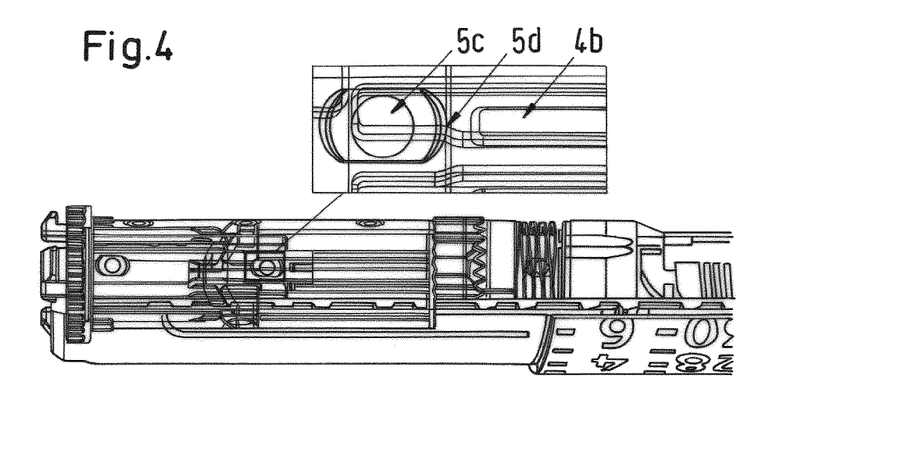
FIG. 4 shows a further enlarged detail of the dose setting mechanism of FIG. 1 with a dose dialed and with the dose button released (i.e. in the dose dialing mode),\
Figure 5:
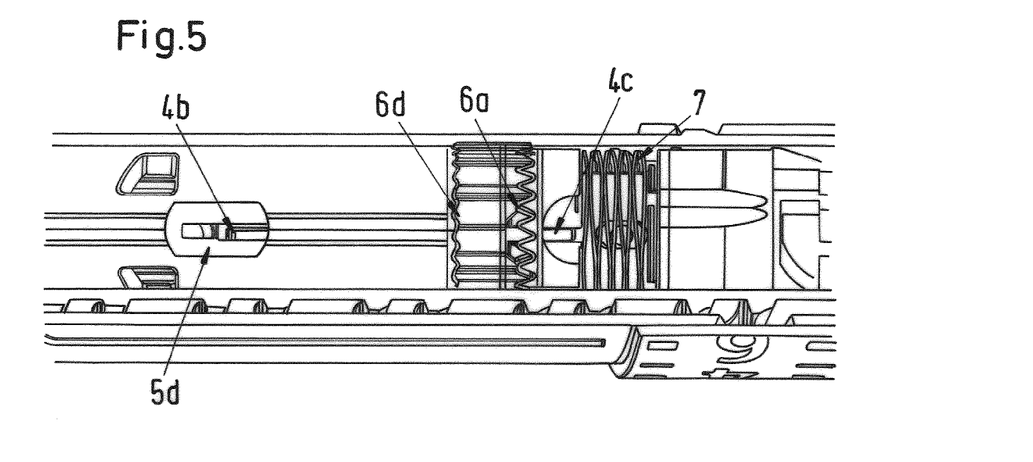
FIG. 5 shows a further enlarged detail of the dose setting mechanism of FIG. 4.
Figure 6:
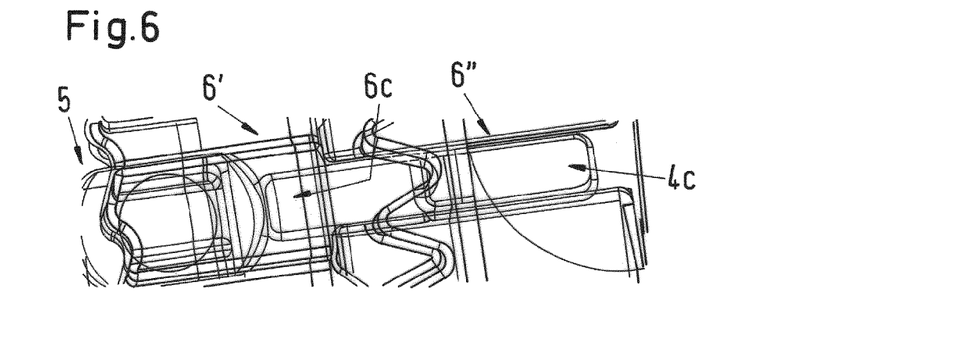
FIG. 6 shows a further enlarged detail of the dose setting mechanism of FIG. 1, 2 or 3.

Such a feature is shown in FIGS. 3 to 5 where the second clutch element 5 is keyed to the proximal drive member 4" by means of longitudinally directed splines 4b formed on the proximal drive member 4" engaging corresponding grooves 5c of the second clutch 5 to prevent relative rotation between the clutch member 5 and the drive member 4, while allowing relative longitudinal movement there between. In the grooves 5c steps 5d are provided so as to prevent proximal movement of the proximal drive member 4" only during normal reset. In other words, grooves 5c have a distal portion of larger width and a proximal portion of smaller width with the step 5d located at the transition between these two portions. Thus, depending on the axial arrangement of the spline 4b within the groove 5c proximal movement of the spline 4b is either stopped by step 5d or allowed guiding the spline 4b in the portion of the groove 5c with the smaller width. As an alternative the spline(s) 4b may be provided on the tubular element of the second clutch and the groove(s) 5c may be provided on the proximal drive member.

In order to ensure the step 5d in the second clutch groove 5c engages with the spline 4b of the drive sleeve proximal end 4" so as to prevent the drive sleeve sliding proximally during reset, the spline 4b on the drive sleeve must be biased into the step 5d in the second clutch. This is achieved through the angled faces of the toothed engagement of the second clutch (teeth 5e) and the first clicker 6' (teeth 6d), the toothed engagement of the first and second clicker components 6', 6" and the splined engagement of the second clicker 6" and the proximal drive member 4". In other words, the angled teeth (5e, 6d) between the first clicker 6' will tend to introduce relative rotation between the second clutch 5 and proximal drive member 4", within the limits of the fits of the other toothed or splined engagements, such that the spline 4b is biased towards the step 5d during resetting of the device, or whenever the user has released the dose button.

To increase robustness of the clicker mechanism against user abuse, it is preferred to form the splines 4c of the proximal drive member 4" and/or the corresponding grooves 6c of the first clicker component 6', respectively, such that at least one of the splines 4c and the grooves 6c has a rounded form or contour. Therefore when the parts are in the positions shown in FIG. 2 after releasing the dose button following attempting to dispense with a blocked needle, if the user tries to rotate the dose setting member 3, the dialing torque will be significantly higher than the normal torque required to overcome the clicker teeth 6a, 6b, and it should therefore be obvious to the user that something is wrong, e.g. the needle is blocked and the mechanism is jammed. However, if the user continues to try and dial, the rounded splines are allowed to bump underneath the grooves in the first clicker part and will not be plastically deformed and therefore will not cause permanent damage to the device.

As mentioned above, the correct way to overcome this 'misuse' failure mode is to replace the blocked needle, which will relieve the cartridge pressure by releasing medicament through the needle. The user can then prime the device and deliver the required dose.

Summarizing, the proximal movement of the drive sleeve 4 (including the proximal portion 4", possibly a coupler and distal portion 4') is a safety feature designed to overcome a failure mode where the user applies a dispense force to the device without no needle (or a blocked needle) fitted. This creates very high forces in the device (e.g. if the user applies 80N then a 2:1 gear ratio of a mechanism will deliver approximately 160N to the cartridge's rubber stopper). These high forces are sufficient to cause the rubber parts of the cartridge (stopper and septum) to deform elastically (like a giant spring). This deformation creates space for the spindle to advance by a couple of units (~approx 5-10 units) which in turn allows the number sleeve 3 to rotate back (so that the number sleeve now displays 5-10 units less than the 'set' dose without any insulin having been dispensed).

When the user releases the force on the dose dial grip (not shown) the elastic forces in the cartridge press back against the bearing, which can cause the spindle to reset. However, the number sleeve 3 retains in now decreased number (approx. 5-10 units below the set dose). When the spindle moves back, resetting the device, the pressure in the cartridge is released. Therefore the entire process can be repeated. With every 'dose' the number displayed in the dose window by the number sleeve 3 will decrease by 5-10 units. Eventually the number sleeve 3 will return to 0 without any insulin having been dispensed.

The solution to the problem is to allow the entire drive sleeve 4 to move proximally (i.e. towards the dose dial grip) when very high loads are applied to the spindle. However, under normal resetting loads this is not desirable because if the entire drive sleeve 4 moves together proximally then the distal and proximal drive sleeves 4', 4" do not have relative axial movement and therefore do not disengage to allow reset. Under normal resetting loads (typically 2-4N) the proximal drive sleeve portion 4" must be prevented from moving proximally. To ensure that this happens the grooves 5c on the clutch 5, that engage ribs (splines 4b) on the proximal portion 4" of the drive sleeve 4, each have a small step 5d to provide a reaction force to resist movement of the proximal drive sleeve 4". The biasing force of the spring 7 and the shallow biasing teeth on the end of the first clicker component 6' ensure that the splines 4b of the proximal drive sleeve 4" are always rotated (biased) against the side of the clutch grooves 5c that contains this step 5d.

Under normal reset loads (2-4N) the only force tending to move the proximal drive sleeve 4" in the proximal direction is friction between the distal drive sleeve 4' (or its coupler) and proximal drive sleeve 4". In this instance proximal movement of the proximal drive sleeve 4" is also resisted by friction between the proximal drive sleeve 4" and the clutch 5, first and second clicker parts 6', 6", and the dose dial grip. Therefore the small steps 5d are advantageous.

When the user has attempted to dispense a dose with no needle fitted the dose dial grip has already been pressed in and therefore the clutch 5 and hence step 5d on the side of the clutch splines has already moved distally relative to the end of the proximal drive sleeve splines. Therefore when the user lets go of the dose dial grip, the drive sleeves 4', 4" and clutch 5 plus dose dial grip can all move proximally together and will do so under the compressive force from the bung on the piston rod and hence distal drive sleeve 4'. So in this case the step 5d in the clutch is not relevant as there is no relative movement between the proximal drive sleeve and clutch.

The dose setting mechanism may be part of an injection device further comprising a cartridge containing a medicament. The cartridge may be held in a cartridge holder which can be permanently or releasably attached to the dose setting mechanism.

The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5-des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDahttp://en.wikipedia.org/wiki/Dalton_%28unit %29) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A dose setting mechanism for a drug delivery device, the mechanism comprising:
   a dose setting member,
   a drive member, for driving a piston rod in a distal direction during dose dispensing, the drive member comprising a proximal drive member and a distal drive member,
   a first clutch for releasably coupling the proximal drive member and the distal drive member,
   spring means for biasing the proximal drive member and the distal drive member in the coupled state during dose setting and dose dispensing, and
   engaging means associated to the proximal drive member and to the dose setting member,
   characterized in that the engaging means comprises hooks provided on fingers protruding from the proximal end of the proximal drive member and
   a corresponding inwardly protruding flange on the proximal end of the dose setting member
   such that the proximal drive member entrains the dose setting member in the distal direction during dose dispensing
   but allows a relative axial movement of the proximal drive member with respect to the dose setting member in a proximal direction.

2. A dose setting mechanism according to claim 1, characterized in that the mechanism is a resettable mechanism further comprising a dose button for transmitting a dispensing force applied by a user to the mechanism, wherein the engaging means allow a relative axial movement of the proximal drive member with respect to the dose setting member in the proximal direction only when the dose button is pressed during or following dose dispense, and resists relative axial movement when the dose button is not depressed during reset.

3. A dose setting mechanism according to claim 1, characterized in that the first clutch rotationally couples the proximal drive member and the distal drive member during dose setting and dose dispensing and rotationally decouples the proximal drive member and the distal drive member during resetting of the mechanism.

4. A dose setting mechanism according to claim 1, characterized in that, when the proximal drive member is not moved in the proximal direction with respect to the dose setting member then the first clutch will rotationally decouple permitting reset of the piston rod.

5. A dose setting mechanism according to claim 1, further comprising a second clutch for releasably coupling the proximal drive member and the dose setting member, characterized in that the second clutch comprises a tubular element having at least one axial groove engaging a spline provided on proximal drive member.

6. A dose setting mechanism according to claim 5, characterized in that the at least one axial groove is provided with a step which is located at a transition from a first portion of the groove having a smaller width to a second portion of the groove having a larger width, wherein the width of the spline is chosen to allow the spline to slide within both portions of the groove.

7. A dose setting mechanism according to claim 6, characterized in that the a step in the axial groove prevents proximal movement of the proximal drive member during resetting.

8. A dose setting mechanism according to claim 5, further comprising means for biasing and/or holding the spline in an angular position with respect to the groove.

9. A dose setting mechanism according to claim 8, characterized in that the means for biasing and/or holding the spline comprise a clicker mechanism for releasably coupling the second clutch and the proximal drive member during resetting of the mechanism.

10. A dose setting mechanism according to claim 9, characterized in that the clicker mechanism comprises two clicker parts, the first clicker part being rotationally releasably coupled to the clutch, the second clicker part being rotationally fixed to the proximal drive member and the two clicker parts being rotationally releasably coupled to each other.

11. A dose setting mechanism according to claim 9, characterized in that the first clicker part is rotationally fixed to the proximal drive member by a clicker spline engaging a corresponding clicker groove, wherein the clicker spline and/or the clicker groove has a rounded outline.

12. A dose setting mechanism according to claim 1, characterized in that the second clutch rotationally couples the dose setting member and the drive member during dose setting and rotationally decouples the dose setting member and the drive member during dose dispensing.

13. An injection device comprising the dose setting mechanism according to claim 1 and a medicament which is preferably contained in a cartridge.

* * * * *